United States Patent [19]

McNair

[11] 4,285,343
[45] Aug. 25, 1981

[54] SANITARY NAPKIN

[76] Inventor: Rosetta M. McNair, 3013 Guinevere Dr., Chespeake, Va. 23323

[21] Appl. No.: 85,423

[22] Filed: Oct. 16, 1979

[51] Int. Cl.$^3$ .............................................. A61F 13/16
[52] U.S. Cl. .................................................. 128/287
[58] Field of Search ............ 128/287, 289, 284, 290 R

[56] References Cited

U.S. PATENT DOCUMENTS

| | | | |
|---|---|---|---|
| 2,102,359 | 12/1937 | Frieman | 128/289 |
| 2,787,271 | 4/1957 | Clark | 128/290 R |
| 2,890,701 | 6/1959 | Weinman | 128/289 |
| 3,881,490 | 5/1975 | Whitehead et al. | 128/287 |

Primary Examiner—John D. Yasko
Attorney, Agent, or Firm—William F. Frank

[57] ABSTRACT

The present invention provides a central elongate highly-absorptive pad element having side panels extending laterally therefrom. The side panels may be formed as an integral part of the invention or may be formed separately and secured to the longitudinal edges of the central element. The lines of common juncture between the central element and the side panels provides flexibility so that the side panels may be folded over the upper surface of the central element for packaging and may be folded toward the back side of the central element when the invention is used. The central element and the side elements have a fluid-impervious backing upon which is placed a thin layer of flexible adhesive which will not penetrate the absorbent materials placed thereon. The central element has a highly-absorptive pad means whereas the absorptive means on the side panels may be minimal. The backing element of the central portion of the invention contains a strip of adhesive covered by a protective tape until use. A similar arrangement is provided on each of the side panels. When used, the central element is placed on the inner side of the undergarment after the protective strip has been removed. The side panels are then folded over the outer surface of the undergarment, one side panel engaging the outer surface of the undergarment, the other side panel engaging the absorptive surface of the first fold of the pad. The side panels may be of a width such that when folded over the central panel they meet along a common line rather than overlap.

3 Claims, 7 Drawing Figures

SANITARY NAPKIN

FIELD OF THE INVENTION

The present invention is in the field of absorbent articles, and more particularly, is in the field of absorbent pads for use by women during periods of menstruation.

BACKGROUND OF THE INVENTION AND PRIOR ART

Absorbent pads for use by women during menstrual periods have advanced over the years from the familiar Kotex type pad requiring the use of a special small belt through the Tampon development and into the present day flat, but highly-absorptive pads which generally are constructed so as to be removably attached, generally through an adhesive application, to the undergarment. Throughout the evolution, emphasis has been placed upon a highly-absorptive article but one which was also less and less conspicuous, particularly when worn under outer-garments which, by design and fashion, may be close fitting. Currently, the elongated, flat pad having a maximum absorptive quality is available. The absorptive quality of available pads can be selected depending upon the requirement for absorption. The absorptive qualities appear to vary from that of minimal-absorptive needs designed for daily wear to the highly-absorptive pad required by women having a copious menstrual flow.

While the pads designed for maximum absorptive quality have been found generally acceptable, it has been also found that these pads provide less than the desired amount of protection. The maximum-absorptive pads do not always prevent the staining of the undergarments by the menstrual fluid and this is very difficult to remove. Additionally, the design of the pads does not maintain them in the desired position when worn and they tend to fold along their longitudinal axis which is believed also tends toward aiding in the staining of undergarments.

SUMMARY OF THE PRESENT INVENTION

The present invention is an improvement over the current art in that it provides an absorptive pad which will not fold or crumple laterally along the longitudinal axis but will remain substantially flat or slightly concave to conform to the body surface. It has also been found that this improvement presents staining of undergarments and has actually increased absorptive capacity.

BRIEF DESCRIPTION OF THE DRAWINGS

The present invention will now be shown by way of illustrative embodiment only in the accompanying drawings wherein.

DETAILED DESCRIPTION OF THE INVENTION

Figure 1:
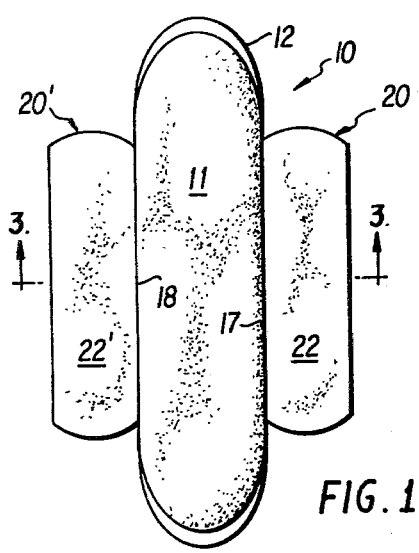
FIG. 1 is a plan view of the absorptive pad of the present invention.
Figure 2:
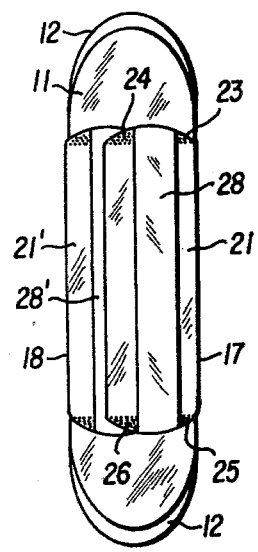
FIG. 2 is a bottom plan view of the invention shown in FIG. 1 as the invention might be packaged or as it is arranged in the installation on an undergarment.
Figure 3:
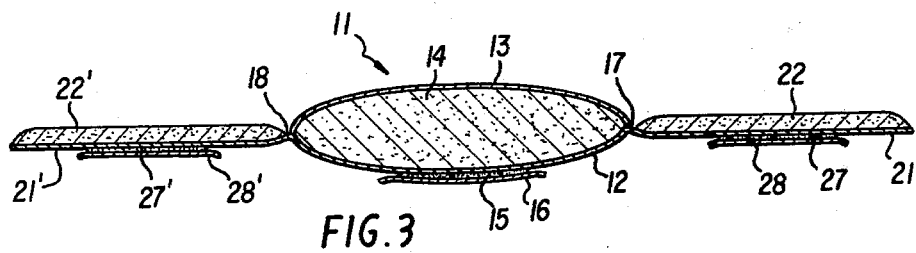
FIG. 3 is an elevation view in cross-section along the plane 3—3 of FIG. 1.

The present invention is indicated generally as 10 in FIG. 1. The invention comprises a central elongate absorbent element 10 with laterally extending side panels 20 and 21. On element 10 is an elongated absorbent pad 11. Pad 11 comprises a fluid impervious backing element 12 on which an absorbent means is secured thereto by a light overall layer of flexible adhesive which does not penetrate the absorbent means. The absorbent means, as perhaps better seen in FIG. 3 comprises a fluid pervious cover sheet 13 and a central absorbent bat 14, the cover sheet and absorbent bat being of conventional construction for this type of use. It will be noted in FIG. 1 that the absorbent means does not fully cover the backing element at the distal extremities thereof in order to provide a more tapered fit as is customary and desired in this art. Panels 20 and 20' extend laterally along respective longitudinal edges 17 and 18 of the absorbent pad 11 in centerized relationship therewith and are from one-half to three-quarters the length of element 11, preferably about two-thirds. These are identical and the description thereof will be confined to panel 20, it being understood that panel 20' is identical in construction. Panel 20 comprises a fluid-impervious backing element 21 as can be seen in FIGS. 2 and 3 to which there is secured, by a light overall layer of flexible adhesive, a thin pad 22 of soft absorbent material, the thin pad and backing element of the side panel being coextensive. The side panels 20 and 20' may be formed as an integral part of pad 11. If formed separately, each is secured or attached to the central absorbent pad 11 by adhesive or by sewing or other known means, along the respective edges 17 and 18. In either formation, the lines of common juncture of the side panels with the central element must be flexible so that each side panel may be folded about the respective lateral edge of the central element. As seen in FIG. 2, the side panels 20 and 20' have an elongate strip 28 and 28'. Referring to FIG. 3, the elongate strip 28 covers a thin strip of adhesive material 27 which is applied to the outer surface of the backing element 21. This is to protect the adhesive from drying out until such time as the device is used. As will also be seen in FIG. 3, on the outer surface of the backing element of the central absorbent pad 11 there is a strip 16 substantially identical to strip 28 on side panel 20 which covers and protects a thin strip of adhesive 15 thereon. As seen in FIG. 2, the backing element 21 of side panel 20 may contain perforated or roughened areas 23, 24, 25, and 26 which extend across the entire tip of the outer surface of the backing element, but are covered in FIG. 2 by the ends of the protective strip 28. The purpose of these roughened areas 23-26 is to provide some frictional engagement between the outer surface of an undergarment when the present invention is applied to the undergarment. These roughened areas may be omitted without in any way diminishing the effectiveness of the present invention.

Figure 4:
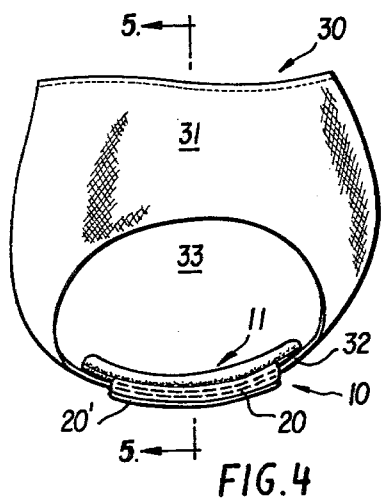
FIG. 4 is an elevation view in partial cross-section showing the present invention installed on an undergarment.
Figure 5:
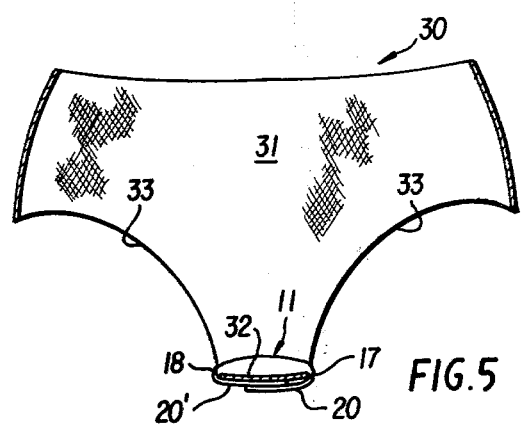
FIG. 5 is an elevation view in partial cross-section along lines 4—4 of FIG. 4.

Referring now to FIGS. 4 and 5, there is shown therein the present invention 10 after it has been applied to an undergarment 30. As can be seen, the undergarment 30 comprises a body support section 31, a leg opening 33 and a crotch section 32. The invention has been applied to the undergarment 30 by removing the protective strip 16 from the outer surface of the backing element 12, thus exposing the adhesive strip 15. The outer surface of the backing element is then placed in contact with the inner surface of the crotch portion 32 of garment 30, the adhesive engaging the material sufficiently to prevent the central element 10 from sliding. The protective strips 28 and 28' are then removed from side panels 20 and 20' thus exposing the adhesive strip on the outer surface of the backing elements 21 and 21'. Depending upon which side element is first folded over the outer surface of the crotch section 32, the adhesive element 27 and 27' engages the outer surface of the crotch element 32 and the adhesive element 27' or 27 then engages the surface of absorbent pad 22 or 22'. As thus placed in the undergarment, the absorbent pad 11 is uppermost and the soft absorbent pads 22 and 22' are below the garment, thus avoiding any possibility of chafing the surfaces of the body in contact with the device.

Figure 6:
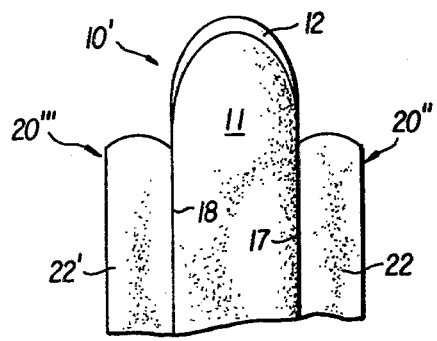
FIG. 6 is a top plan view of another embodiment of the present invention.
Figure 7:
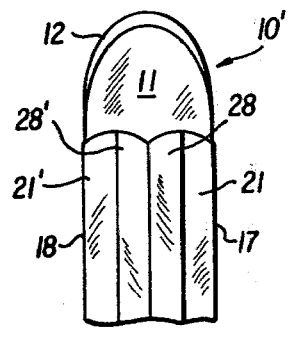
FIG. 7 is a top plan view of the embodiment shown in FIG. 6 with the side panels folded as in the embodiment shown in FIG. 2.

Referring now to FIGS. 6 and 7, it will be noted that this embodiment of the invention differs from that shown in FIGS. 1 and 2 in that the side panels 20" and 21" are only of a width such that when folded over the central pad portion, the outer edges of the side panels meet along the general center line of the outer surface of the backing element of the central pad. This embodiment presents a less thick section in the crotch portion of the undergarment, but it is no less effective.

It has been found that when the present device is placed on the garment in the manner described above, and the garment is worn, the central absorbent pad 11 is maintained in substantially full contact with the body and does not bunch up laterally, but remains in comfortable contact. The central absorbent pad 11 also does not tend to move longitudinally, thereby bringing some discomfort or unwanted attention to the wearer. It has also been found that when so emplaced, the present invention prevents staining of the crotch of the undergarment and more readily completely absorbs the menstrual fluid.

Those of skill in the art will recognize that the size and materials as illustratively disclosed in the above description may be varied according to needs without departing from the principle of the present invention as recited in the appended claims.

What is claimed is:

1. An improved sanitary napkin comprising an elongated central absorptive means with side panel means extending laterally from each longitudinal edge of said central means with a flexible line of juncture therebetween, each said side panel being of a width at least half the width of said central element, a fluid-impervious backing for said central means and for each of said side panels with means on each backing to secure said napkin to an undergarment, said central means being secured to the inner surface of the crotch portion of said undergarment, each side panel being folded over to encompass at least half of the outer surface of said crotch portion to which it is secured, the so-positioned napkin maintaining its longitudinal position and its lateral width as the crotch portion of the undergarment conforms to the body of the wearer.

2. The napkin according to claim 1 wherein said central absorptive means comprises a fluid-impervious backing, a thin layer of flexible adhesive on one surface, a highly-absorptive, fluid-pervious, absorbent material secured to said one surface by said adhesive, and a fluid-pervious cover for said absorptive material, said cover and said absorptive material not being co-extensive with said one surface at the distal ends thereof, the other surface of said backing element having a thin longitudinal strip of an adhesive covered by a removable protective strip.

3. The napkin according to claim 1 wherein each of said side panels comprises a fluid-impervious backing, one surface of which is covered with a thin layer of a flexible adhesive to which a layer of soft, absorbent material is secured thereby, the soft, absorbent material being co-extensive with one surface of the backing, the other surface of said backing having a longitudinal strip of adhesive thereon covered by a removable protective strip.

* * * * *